US012594033B2

(12) United States Patent
Tan et al.

(10) Patent No.: US 12,594,033 B2
(45) Date of Patent: Apr. 7, 2026

(54) PHOTOELECTRIC DETECTOR, PPG SENSOR, AND ELECTRONIC DEVICE

(71) Applicant: HONOR DEVICE CO., LTD., Shenzhen (CN)

(72) Inventors: Yinjiong Tan, Shenzhen (CN); Ruiying Shang, Shenzhen (CN); Bingxin Liu, Shenzhen (CN); Xinpei Cai, Shenzhen (CN)

(73) Assignee: Honor Device Co., Ltd., Shenzhen (CN)

( * ) Notice: Subject to any disclaimer, the term of this patent is extended or adjusted under 35 U.S.C. 154(b) by 0 days.

(21) Appl. No.: 18/043,841

(22) PCT Filed: Sep. 1, 2022

(86) PCT No.: PCT/CN2022/116614
§ 371 (c)(1),
(2) Date: Mar. 2, 2023

(87) PCT Pub. No.: WO2023/103485
PCT Pub. Date: Jun. 15, 2023

(65) Prior Publication Data
US 2024/0324955 A1 Oct. 3, 2024

(30) Foreign Application Priority Data
Dec. 7, 2021 (CN) .......................... 202111485328.3

(51) Int. Cl.
*A61B 5/00* (2006.01)
*A61B 5/024* (2006.01)
*A61B 5/1455* (2006.01)

(52) U.S. Cl.
CPC .......... *A61B 5/681* (2013.01); *A61B 5/02433* (2013.01); *A61B 5/14552* (2013.01); *A61B 2562/0238* (2013.01)

(58) Field of Classification Search
CPC . A61B 5/681; A61B 5/02433; A61B 5/14552; A61B 2562/0238;
(Continued)

(56) References Cited

U.S. PATENT DOCUMENTS 9,526,431 B2 12/2016 Zakharov et al.
10,433,739 B2 10/2019 Weekly et al.
(Continued)

FOREIGN PATENT DOCUMENTS

CN 206565935 U 10/2017
CN 107595297 A 1/2018
(Continued)

*Primary Examiner* — Abid A Mustansir
(74) *Attorney, Agent, or Firm* — Fish & Richardson P.C.

(57) ABSTRACT

A photoelectric detector, a PPG sensor, and an electronic device are provided. The photoelectric detector includes a photo diode, configured to sense light on a first band, a second band, and a third band; at least one first optical filter part, located on the photo diode, and configured to transmit light on the first band and the second band, and block light on the third band; and at least one second optical filter part, located on the photo diode, and configured to transmit the light on the third band and block the light on the first band and the second band.

20 Claims, 5 Drawing Sheets

(58) Field of Classification Search
CPC ........ A61B 2562/0233; A61B 5/02427; A61B
5/02416; A61B 5/02
See application file for complete search history.

(56) References Cited

U.S. PATENT DOCUMENTS

| | | | |
|---|---|---|---|
| 11,546,537 B2 | 1/2023 | Nakata | |
| 11,557,144 B2 | 1/2023 | Lin et al. | |
| 11,723,563 B1* | 8/2023 | Shaga ................... | A61B 5/681 |
| | | | 600/336 |
| 2004/0080638 A1 | 4/2004 | Lee | |
| 2017/0311825 A1 | 11/2017 | Weekly et al. | |
| 2018/0303359 A1 | 10/2018 | O'Brien et al. | |
| 2021/0059585 A1 | 3/2021 | Choi et al. | |
| 2021/0306542 A1 | 9/2021 | Kulcke et al. | |
| 2022/0039708 A1 | 2/2022 | Arias et al. | |
| 2022/0240822 A1* | 8/2022 | Takayama .......... | A61B 5/14552 |
| 2022/0248968 A1 | 8/2022 | Xi et al. | |

FOREIGN PATENT DOCUMENTS

| | | | |
|---|---|---|---|
| CN | 109065721 A | 12/2018 | |
| CN | 109195510 A | 1/2019 | |
| CN | 110137196 A | 8/2019 | |
| CN | 110393514 A | 11/2019 | |
| CN | 210871603 U | 6/2020 | |
| CN | 112686216 A | 4/2021 | |
| CN | 113288128 A | 8/2021 | |
| EP | 2563012 B1 | 3/2015 | |
| EP | 2768391 B1 | 5/2019 | |
| WO | 2016079379 A1 | 5/2016 | |
| WO | 2020150224 A2 | 7/2020 | |

* cited by examiner

100

243 244

PHOTOELECTRIC DETECTOR, PPG SENSOR, AND ELECTRONIC DEVICE

CROSS-REFERENCE TO RELATED APPLICATIONS

This application is a national stage of International Application No. PCT/CN2022/116614, filed on Sep. 1, 2022, which claims priority to Chinese Patent Application No. 202111485328.3, filed on Dec. 7, 2021. The disclosures of the aforementioned applications are hereby incorporated by reference in their entireties.

TECHNICAL FIELD

This application relates to the field of biological sensing, and in particular, to a photoelectric detector, a photo plethysmo graph (photo plethysmo graph, PPG) sensor, and an electronic device.

BACKGROUND

In an existing PPG sensor applied to an electronic device for sensing physiological characteristics of a user, a problem of a low signal-to-noise ratio exists.

SUMMARY

According to a first aspect, this application provides a photoelectric detector, including:
- a photo diode, configured to sense light on a first band, a second band, and a third band;
- at least one first optical filter part, located on the photo diode, and configured to transmit light on the first band and the second band and block light on the third band; and
- at least one second optical filter part, located on the photo diode, and configured to transmit the light on the third band and block the light on the first band and the second band.

The photoelectric detector is configured with a first optical filter part and a second optical filter part, so that detection of light on the first band and the second band by the photo diode is relatively decoupled from detection of light on the third band. To be specific, the photoelectric detector may detect the light on the first band and the second band based on a region in which the photo diode is provided with the first optical filter part, and detect the light on the third band based on a region in which the photo diode is provided with the second optical filter. In addition, when the photoelectric detector detects the light on the first band and the second band, the light on the third band is blocked by the first optical filter and cannot be incident into the photo diode. This can avoid impact of the light on the third band, reduce noise in detecting the light on the first band and the second band, and increase a signal-to-noise ratio in detecting the light on the first band and the second band. Similarly, when the photoelectric detector detects the light on the third band, the light on the first band and the light on the second band are blocked by the first optical filter and cannot be incident into the photo diode. This can avoid impact of the light on the first band and the second band, reduce noise in detecting the light on the third band, and increase a signal-to-noise ratio in detecting the light on the third band.

In some embodiments, the first band is on a red light spectrum, the second band is on an infrared light spectrum, and the third band is on a green light spectrum. That is, red light, infrared light, and green light can be sensed by the photo diode. The first optical filter part may selectively transmit the red light and the infrared light and block the green light. The second optical filter part may selectively transmit the green light and block the red light and the infrared light. Therefore, that is of the photo diode and that is covered by the first optical filter may receive the red light and the infrared light, but receives no green light; and a region that is of the photo diode and that is covered by the second optical filter may receive green light, but receives neither the red light nor the infrared light.

In some embodiments, in a thickness direction of the photo diode, a ratio of an area of a projection of the at least one first optical filter part on the photo diode to an area of a projection of the at least one second optical filter part on the photo diode is 1:(1.6~1.3). The photo diode is a full-spectrum sensitive photo diode, and sensitivity of the photo diode to the red light and the infrared light and that of the photo diode to the green light are different. Specifically, a ratio of the sensitivity of the photo diode to the red light and the infrared light to that of the photo diode to the green light is approximately (1.6~1.3): 1. To be specific, when a same photo diode receives the red light and the infrared light at a light irradiance of 1 mW/cm$^2$, and receives the green light at a light irradiance of 1 mW/cm$^2$, a ratio of photo-generated current by the red light and the infrared light to photo-generated current by the green light is (1.6~1.3): 1. Therefore, in some embodiments, the ratio of the total area of projections of all the first optical filter parts on the photo diode to a total area of projections of all the second optical filter parts on the photo diode is 1:(1.6~1.3). In this way, the photo-generated current generated by the photoelectric detector for the received red light and infrared light at a light irradiance of 1 mW/cm$^2$, is approximately equal to the photo-generated current generated by the photoelectric detector for the received green light irradiated at a light irradiance of 1 mW/cm$^2$.

In some embodiments, a quantity of the first optical filter parts is the same as a quantity of the second optical filter parts. In the thickness direction of the photo diode, a ratio of an area of a projection of each first optical filter part on the photo diode to an area of a projection of each second optical filter part on the photo diode is 1:(1.6~1.3). In some other embodiments, in the thickness direction of the photo diode, the area of the projection of each first optical filter part on the photo diode is the same as the area of the projection of each second optical filter part on the photo diode, and a ratio of a quantity of the first optical filter parts to a quantity of the second optical filter parts is 1:(1.6~1.3). To be specific, a ratio of a total area of all the first optical filter parts to a total area of all the second optical filter parts may be adjusted by adjusting a quantity of the first optical filter parts and second optical filter parts or a size of the area of each first optical filter part and each second optical filter part.

In some embodiments, a plurality of first optical filter parts and a plurality of second optical filter parts are arranged in a matrix with a plurality of rows and columns. In the plurality of rows and columns, one first optical filter part and one second optical filter part are arranged alternately and cyclically in each row, and one first optical filter part and one second optical filter part are arranged alternately and cyclically in each column.

In some embodiments, in the thickness direction of the photo diode, a projection of the first optical filter part on the photo diode is a rectangle, and a projection of the second optical filter part on the photo diode is a rectangle. In other embodiments, shapes and arrangement rules of the first optical filter part and the second optical filter part are not limited thereto.

In some embodiments, a quantity of the first optical filter parts is the same as a quantity of the second optical filter parts. In the thickness direction of the photo diode, a width of the rectangle formed by the projection of the first optical filter part on the photo diode is the same as a width of the rectangle formed by the projection of the second optical filter part on the photo diode, and a length ratio of the rectangle formed by projection of the first optical filter part on the photo diode to that of the second optical filter part on the photo diode is 1:(1.6~1.3).

In some embodiments, the photoelectric detector further includes a circuit substrate, and the photo diode is electrically connected to the circuit substrate. The circuit substrate is, for example, a printed circuit board, the photo diode is electrically connected to the circuit substrate by using a lead, and the lead is, for example, a gold wire, but this is not limited herein.

In some embodiments, the photoelectric detector further includes a packaging layer, and the packaging layer coats the photo diode, the first optical filter part, and the second optical filter part. A material of the package layer is, for example, an epoxy resin, but this is not limited herein.

According to a second aspect, this application provides a PPG sensor, including:

the photoelectric detector according to the first aspect.

a first light source, configured to send a first optical signal, where at least a part of light obtained after the first optical signal is reflected by skin/a tissue of a user is on a first band;

a second light source, configured to send a second optical signal, where at least a part of light obtained after the second optical signal is reflected by the skin/tissue of the user is on a second band; and a third light source, configured to send a third optical signal, where at least a part of light obtained after the third optical signal is reflected by the skin/tissue of the user is on a third band; where the photoelectric detector is configured to receive light on the first band and generate a first PPG signal, receive light on the second band and generate a second PPG signal, and receive light on the third band and generate a third PPG signal, where the first PPG signal, the second PPG signal, and the third PPG signal are used to detect physiological characteristics of the user.

The PPG sensor includes the photoelectric detector according to the first aspect. Because the photoelectric detector is provided with a first optical filter part and a second optical filter part, detection of light on the first band and the second band by the photo diode is relatively decoupled from detection of light on the third band. To be specific, the photoelectric detector may detect the light on the first band and the second band based on a region in which the photo diode is provided with the first optical filter part, and detect the light on the third band based on a region in which the photo diode is provided with the second optical filter. In addition, when the photoelectric detector detects the light on the first band and the second band, the light on the third band is blocked by the first optical filter and cannot be incident into the photo diode. This can avoid impact of the light on the third band, reduce noise in detecting the light on the first band and the second band, increase a signal-to-noise ratio in detecting the light on the first band and the second band, and improve accuracy in detecting the first PPG signal and the second signal. Similarly, when the photoelectric detector detects the light on the third band, the light on the first band and the light on the second band are blocked by the first optical filter and cannot be incident into the photo diode. This can avoid impact of the light on the first band and the second band, reduce noise in detecting the light on the third band, increase a signal-to-noise ratio in detecting the light on the third band, and improve accuracy in detecting the third signal. In this way, data of the physiological feature of the user detected based on the first PPG signal, the second PPG signal, and the third PPG signal is more accurate.

In some embodiments, the PPG sensor includes a light source group, the light source group includes a first light source, a second light source, and a third light source, and a plurality of photoelectric detectors are spaced around the light source group. The plurality of photoelectric detectors are disposed around the light source group to detect a PPG signal. In this way, on one hand, PPG signals in a plurality of position directions can be obtained, so that a problem that a detection result is inaccurate due to a difference of a biological tissue or wear habit of a user can be avoided; on the other hand, a PPG signal with good signal quality can be selected from PPG signals in a plurality of location directions, thereby improving accuracy in detecting biological information of the user.

In some embodiments, the PPG sensor includes a plurality of light source groups that are spaced. By disposing the plurality of light source groups, the photoelectric detector can detect light from different light source groups. This can avoid a problem that a detection result is inaccurate due to the difference of the biological tissue or the wear habit of the user, thereby improving the accuracy in detecting the biological information of the user.

In some embodiments, physiological characteristics includes oxygen saturation and a heart rate. The first optical signal is red light, the second optical signal is infrared light, and the first PPG signal and the second PPG signal are used to detect oxygen saturation of the user. The third optical signal is green light, and the third PPG signal is used to detect the heart rate of the user. The is mainly measured by using green light, because a PPG detected by green light has a high signal-to-noise ratio, requirements for detection and signal conditioning are low, and even if there is some interference (for example, motion), the interference can be easily eliminated. The oxygen saturation is mainly measured by using the red light and the infrared light, because hemoglobin and oxygenated hemoglobin in blood have different absorption rates of the red light and the infrared light: The oxygenated hemoglobin absorbs more near infrared light (about 900 nm), while the hemoglobin absorbs more red light (about 650 nm). The absorption difference between the red light and the infrared light can be used to measure the oxygen saturation. Therefore, a PPG signal of the oxygenated hemoglobin and a PPG signal of the human body part may be separately detected by using red light and near infrared light, and then a ratio of the oxygenated hemoglobin to the hemoglobin is obtained based on the PPG signals. In this way, the oxygen saturation of the human body part is obtained.

According to a third aspect, this application provides an electronic device, including the PPG sensor according to the second aspect. The electronic device may be a wrist wearable device (for example, a smartwatch and a smart band), a head mounted device (for example, a smart helmet), a clothing-type device (for example, smart clothing, a smart glove, or a smart arm band). The electronic device may also be a device with a health detection function, such as an oxygen saturation meter or a heart rate detector.

DESCRIPTION OF REFERENCE SIGNS OF MAIN COMPONENTS

Figure 1:
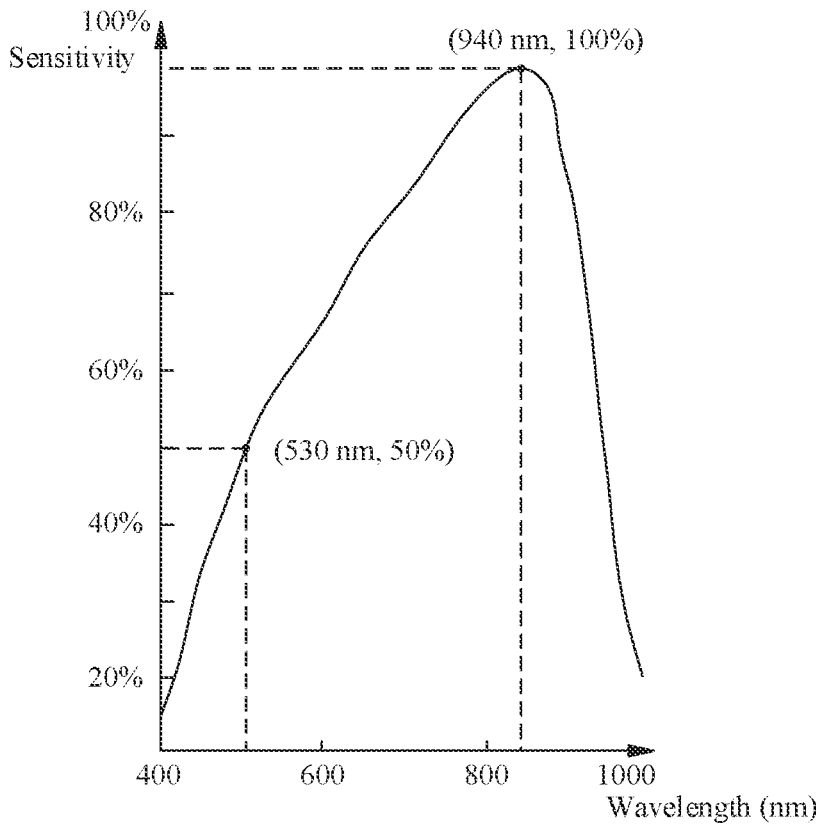
FIG. 1 is a schematic diagram showing a relationship between sensitivity of a photoelectric detector and a wavelength in a conventional technology.

| | |
|---|---|
| Electronic device | 100 |
| Watch band | 12 |
| Watch body | 14 |
| PPG sensor | 20 |
| Light source group | 22 |
| First light source | 221 |
| Second light source | 222 |
| Third light source | 223 |
| Photoelectric detector | 24 |
| Circuit substrate | 241 |
| Photo diode | 242 |
| First optical filter part | 243 |
| Second optical filter part | 244 |
| Lead | 245 |
| Packaging layer | 246 |

DESCRIPTION OF EMBODIMENTS

A pulse wave is a waveform of a volume change of a blood vessel generated when the heart pumps blood. A photo plethysmo graph (photo plethysmo graph, PPG) tracing method is a method in which a corresponding PPG signal is recorded by measuring attenuated light that is reflected and absorbed by blood and a tissue of a human body, and physiological characteristics such as a heart rate or oxygen saturation of a user is calculated based on the PPG signal. A sensor that detects, by using the PPG tracing method, a volume change of a blood vessel generated when the heart pumps blood is referred to as a PPG sensor.

The PPG sensor may be applied to a wrist wearable device (for example, a smartwatch or a smart band). When the user wears the smartwatch, the PPG sensor surrounds a wrist of the user, and is located on a side of the watch body that is close to skin of the user, so as to detect the physiological characteristics of the user. Physiological characteristics include, for example, the heart rate and the oxygen saturation. The PPG sensor may also surround another human body part (for example, an ankles or a finger) of the user for being applied to another wearable device. Another wearable apparatus is, for example, a head mounted device (for example, a smart helmet), or a clothing-type device (for example, smart clothing, a smart glove, or a smart arm band).

Specifically, when light is irradiated on a part of the human body, for example, a wrist or a finger, all tissue components absorb the light, so that light intensity after irradiation decreases. The skin, muscle, bone, and vein are non-pulsatile tissue components, and light absorption is basically stable, for example, an optical path keeps stable. Arteries are pulsatile, and their blood volumes change cyclically with pulsation of the heart. When the heart contracts, the heart pumps blood and the blood volume increases; and when the heart relaxes, the heart returns blood and the blood volume decreases. Therefore, due to the change of the blood volume, absorption of light by the pulsatile part of the arteries changes, and light intensities are different, for example, the optical paths are different. Because absorption of light by the arteries changes, while absorption of light by other tissue components basically remains unchanged, when a light beam is irradiated on a part of the human body such as a wrist or a finger, reflected light cyclically changes in light intensity, and a pulse signal of a photo voltaic pulse wave, that is, the PPG signal, is obtained; and then biological information of the user such as the heart rate or the oxygen saturation can be detected based on the PPG signal.

Using the heart rate as an example, filtering processing is performed on an original PPG signal to obtain a quantity of peaks in a specific time period, and a value of the heart rate of the user can be obtained based on the quantity of peaks.

Using the oxygen saturation as an example, oxygen saturation refers to a percentage of oxygenated hemoglobin $HbO2$ in blood of the human body to all combinable hemoglobin (Hb), that is, oxygen concentration in blood, and may be determined by using formula $SaO2=HbO2/(HbO2+Hb)$. $SaO2$ is the oxygen saturation. $HbO2$ is the oxygenated hemoglobin, and Hb is the hemoglobin.

In addition, an existing PPG method usually uses green light to measure the heart rate, and uses red light and infrared light to measure the oxygen saturation. To be specific, the existing PPG method uses different optical wavelengths to measure the heart rate and the oxygen saturation.

Specifically, the is mainly measured by using green light, because a PPG detected by green light has a high signal-to-noise ratio, a requirement for detection and signal conditioning is low, and even if there is some interference (for example, motion), the interference can be easily eliminated. The oxygen saturation is mainly measured by using the red light and the infrared light, because hemoglobin and oxygenated hemoglobin in blood have different absorption rates of the red light and the infrared light: The oxygenated hemoglobin absorbs more near infrared light (about 900 nm), while the hemoglobin absorbs more red light (about 650 nm). The absorption difference between the red light and the infrared light can be used to measure the oxygen saturation. Therefore, a PPG signal of the oxygenated hemoglobin and a PPG signal of the human body part may be separately detected by using red light and near infrared light, and then a ratio of the oxygenated hemoglobin to the hemoglobin is obtained based on the PPG signals. In this way, the oxygen saturation of the human body part is obtained. For example, the human body part is a wrist or a finger, two light beams with different peak wavelengths, such as red light with a peak wavelength of 650 nm and infrared light with a peak wavelength of 940 nm are used for detection. When the red light and the infrared light pass through the wrist or the finger, corresponding PPG signals of the oxygenated hemoglobin and the hemoglobin are obtained based on different absorption of the oxygenated hemoglobin and the hemoglobin of the two types of light. A corresponding ratio of the oxygenated hemoglobin to the hemoglobin is obtained based on the PPG signal, and the oxygen saturation of the wrist or the finger is obtained based on the ratio.

Therefore, the PPG sensor that has a function of detecting the heart rate and the oxygen saturation usually includes a light emitting diode (Light Emitting Diode, LED) that emits green light, a LED that emits red light, a LED that emits infrared light, and a photoelectric detector. The photoelectric detector is, for example, a photo diode (photo diode, PD).

Figure 2:
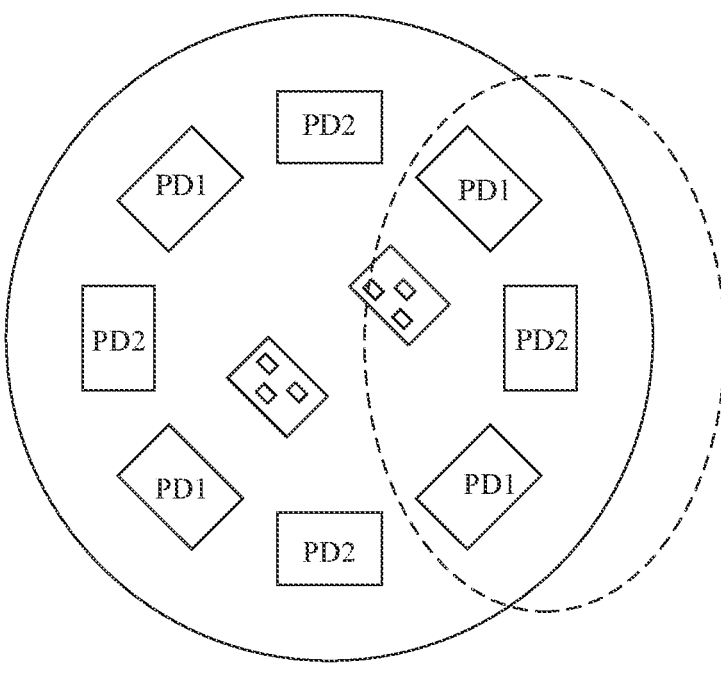
FIG. 2 is a schematic diagram showing distribution of a PPG sensor in an electronic device in another conventional technology.

The following describes main problems with an existing PPG sensor with reference to FIG. 1 and FIG. 2.

As shown in FIG. 1, in the conventional technology, a photoelectric detector (for example, a PD) that receives attenuated light is a full-spectrum receiving component that is sensitive to green light, red light, and infrared light. The photoelectric detector is most sensitive to the infrared light on the 940 nm band, but only about 50% sensitivity to the green light on the 530 nm band in which the heart rate function is detected. This greatly affects the sensed signal value of the green light. In addition, when using the green light to measure the heart rate, the photoelectric detector is also interfered with by an infrared signal emitted by the human body and an infrared signal of an external environment. This reduces a signal-to-noise ratio of the heart rate detection. In addition, when the photoelectric detector measures the oxygen saturation by using the red light and the infrared light, the photoelectric detector is also interfered with by the green light signal. This reduces the signal-to-noise ratio of the oxygen saturation detection.

As shown in FIG. 2, in another conventional technology, the PPG sensor uses two photo diodes (PD1 and PD2) with different sensitive wavelengths. The PD1 is sensitive to the red light spectrum and the infrared light spectrum, and the PD2 is sensitive to the green light spectrum. However, there is a problem of a low effective sensing region in this solution. For example, after the green light, the red light, and the infrared light are reflected and absorbed by the blood and a tissue of the human body, a projection on the PPG sensor is shown by a dashed line in FIG. 2. When the green light is used to measure a heart rate, only the PD2 circled by the dashed line is used for detection, and two PD1 circled by the dashed line cannot sense the green light. This causes a weak value of a sensed signal on the green light obtained by the PPG sensor, and reduces a signal-to-noise ratio of the heart rate detection. Similarly, when the red light and the infrared light are used to measure the oxygen saturation, only the two PD2 circled by the dashed line are used for detection, and the PD2 circled by the dashed line cannot sense the red light and the infrared light. This causes a weak value of a sensed signal on the red light and the infrared light obtained by the PPG sensor, and reduces the signal-to-noise ratio of the oxygen saturation detection.

Therefore, embodiments of this application provide a photoelectric detector, a PPG sensor that uses the photoelectric detector, and an electronic device that uses the PPG sensor, so as to resolve the problem of the low signal-to-noise ratio of the existing PPG sensor.

The following clearly and completely describes technical solutions in embodiments of this application with reference to accompanying drawings in embodiments of this application. Apparently, the described embodiments are only some embodiments rather than all of embodiments of this application.

Figure 3:
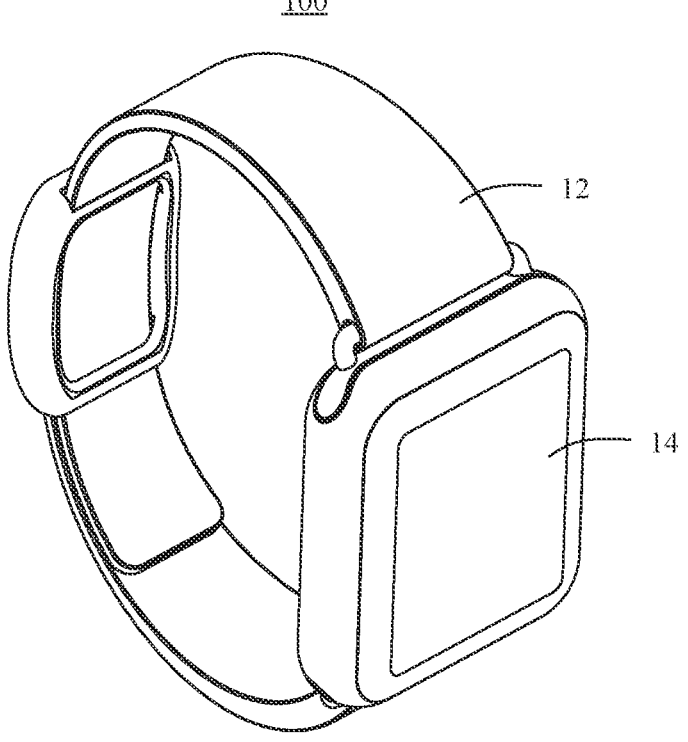
FIG. 3 is a schematic diagram of a structure of an electronic device according to an embodiment of this application.

FIG. 3 is a schematic diagram of a structure of an electronic device according to an embodiment of this application; In FIG. 3, the electronic device 100 is a smartwatch, which includes a watch body 14 and a watch band 12 connected to the watch body 14. A PPG sensor 20 (shown in FIG. 4) is disposed in the watch body 14. When a user wears the smartwatch, the PPG sensor 20 surrounds a wrist of the user and is located on a side of the watch body 14 that is close to the skin of the user, so as to detect physiological characteristics of the user. "Close" may be slightly separated or in direct contact. Physiological characteristics include, for example, the heart rate and the oxygen saturation.

It should be noted that although the heart rate and the oxygen saturation are used as examples for description, a person of ordinary skill in the art should understand that this embodiment of this application can be further used to detect other biological information that is obtained based on the PPG signal, such as blood glucose or blood pressure. This shall also fall within the protection scope of this application.

Figure 4:
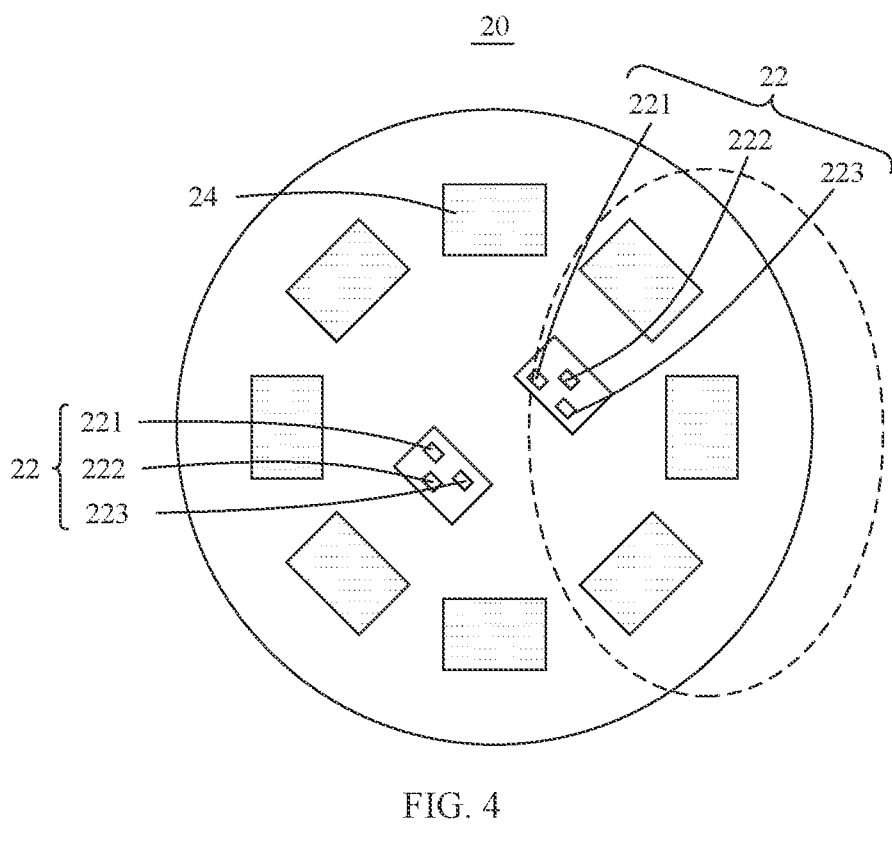
FIG. 4 is a schematic diagram showing distribution of a PPG sensor in an electronic device according to an embodiment of this application.

FIG. 4 is a schematic diagram showing distribution of a PPG sensor in an electronic device according to an embodiment of this application; As shown in FIG. 4, the PPG sensor 20 includes a plurality of light source groups 22 that are spaced and a plurality of photoelectric detectors 24 disposed around the plurality of light source groups 22. Each light source group 22 includes a first light source 221, a second light source 222, and a third light source 223. In FIG. 4, the outline of the PPG sensor 20 is approximately circular. The two light source groups 22 are located in a circular middle region, and the eight photoelectric detectors 24 are equally spaced around the light source groups 22.

The plurality of photoelectric detectors 24 are disposed around the light source group 22 to detect a PPG signal. In this way, on one hand, light from the different light source groups 22 can be detected to obtain PPG signals in a plurality of position directions, so that a problem that a detection result is inaccurate due to a difference of a biological tissue or wear habit of a user can be avoided; on the other hand, a PPG signal with good signal quality can be selected from PPG signals in a plurality of location directions, thereby improving accuracy in detecting biological information of the user.

In another embodiment, a shape of an outline of the PPG sensor 20, a quantity of light source groups 22, a quantity of photoelectric detectors 24, and arrangement of light source groups 22 and photoelectric detectors 24 are not limited thereto. For example, the outline of the PPG sensor 20 may be an ellipse or a strip. The light source group 22 may include only one group or more than two groups. The photoelectric detector 24 may be four on the upper, lower, left, and right sides of the light source group 22.

Specifically, the first light source 221, the second light source 222, and the third light source 223 are respectively configured to send a first optical signal, a second optical signal, and a third optical signal. At least a part of light reflected by the first optical signal through the skin/tissue of the user is on a first band, at least a part of light reflected by the second optical signal through the skin/tissue of the user is on a second band, and at least a part of light reflected by the third optical signal through the skin/tissue of the user is on a third band. The photoelectric detector 24 is configured to, receive light that is on the first band and that is reflected by the skin/tissue of the user from the first optical signal, and generate a first PPG signal; receive light that is on the second band and that is reflected by blood and a tissue of the user from the second optical signal, and generate a second PPG signal; and receive light that is on the third band and that is reflected by the skin/tissue of the user from the third optical signal, and generate a third PPG signal. The first PPG signal, the second PPG signal, and the third PPG signal are used to detect physiological characteristics of the user.

In some embodiments, the first PPG signal and the second PPG signal are used to detect the oxygen saturation of the user. The first optical signal is red light, and the second optical signal is infrared light. The first light source 221 and the second light source 222 are respectively a light emitting diode (light emitting diode, LED) that emits red light and a LED that emits infrared light. The third PPG signal is used to detect the heart rate of the user. The third optical signal is green light, and the third light source 223 is a LED that emits green light. The LED that emits red light, the LED that emits infrared light, and the LED that emits green light may be jointly disposed in a single package or a single die, or may be separately disposed in separate packages or dies. To be specific, a single package or die may include one light source, or may include two or more light sources that emit light of different colors. For example, the single package or die may include a LED that emits red light, a LED that emits green light, and a LED that emits infrared light.

In some embodiments, the LED that emits red light may emit light with a peak wavelength of 650 nm, the LED that emits green light may emit light with a peak wavelength of 530 nm, and the LED that emits red light may emit light with a peak wavelength of 940 nm, but these are not limited herein.

It can be understood that the electronic device 100 further includes a processor (not shown in the figure) electrically connected to the PPG sensor 20 and a memory (not shown in the figure) that stores instructions that may be executed by the processor. The processor may process the PPG signal generated by the PPG sensor 20. For example, the processor detects the oxygen saturation of the user by processing the first PPG signal and the second PPG signal that are generated by the at least one photoelectric detector 24 (for example, a ratio of oxygenated hemoglobin to hemoglobin based on the first PPG signal and the second PPG signal is determined, and then the oxygen saturation of the target part of the user is obtained). Alternatively, the processor detects the heart rate of the user by processing the third PPG signal generated by the at least one photoelectric detector 24 (for example, the heart rate of the to-be-detected user is determined based on a quantity of peaks in the third PPG signal). In addition, the processor may further process instructions executed in the electronic device 100, where the instructions include the instructions stored in the memory or instructions input by an external input/output apparatus. As a non-transitory computer readable storage medium, the memory may be configured to store a non-transitory software program, a non-transitory computer executable program and module. The processor executes various functional applications and data processing by running the non-transitory software program, instructions, and module that are stored in the memory.

Figure 5:
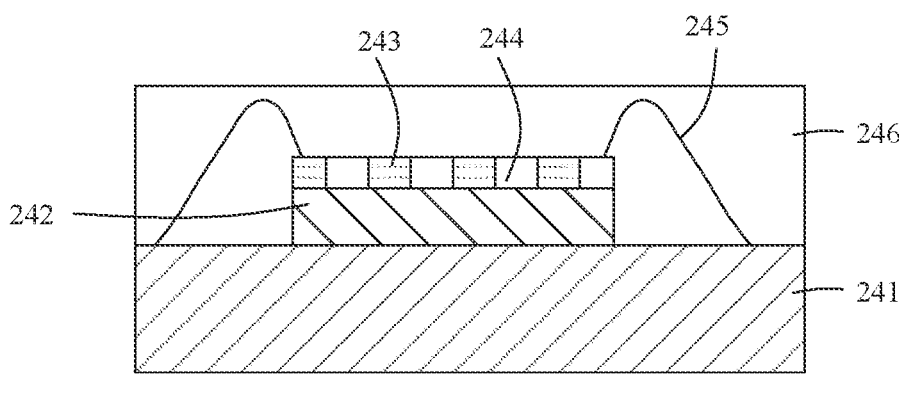
FIG. 5 is a sectional view of a photoelectric detector in FIG. 4.

FIG. 5 is a sectional view of a photoelectric detector in FIG. 4; As shown in FIG. 5, the photoelectric detector 24 includes a circuit substrate 241, a photo diode 242 located on the circuit substrate 241, a first optical filter part 243 and a second optical filter part 244 that are located on the photo diode 242, and a packaging layer 246. The first optical filter part 243 and the optical filter part 244 are located on a side that is of the photo diode 242 and that is away from the circuit substrate 241. The photo diode 242 is electrically connected to the circuit substrate 241 by using a lead 245. The packaging layer 246 coats the photo diode 242, the first optical filter part 243, the second optical filter part 244, and the lead 245. The circuit substrate 241 is, for example, a printed circuit board; the lead 245 is, for example, a gold wire, and a material of the package layer 246 is, for example, an epoxy resin, but these are not limited herein.

Figures 6, 7:
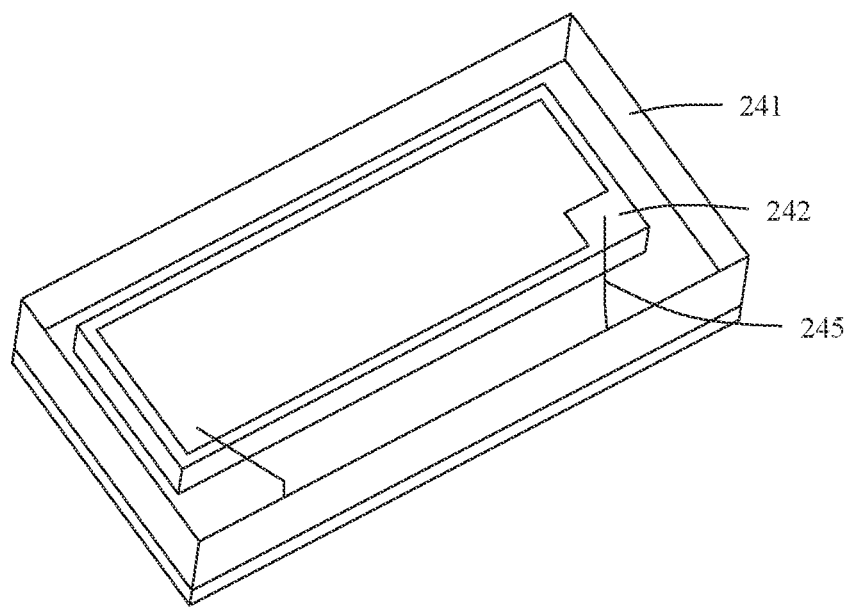
FIG. 6 is a schematic diagram of a structure of a photo diode mounted on a circuit substrate in FIG. 5.
FIG. 7 is a schematic diagram showing layout of a first optical filter part and a second optical filter part in FIG. 5.

FIG. 6 is a schematic diagram of a structure of a photo diode mounted on a circuit substrate in FIG. 5; As shown in FIG. 6, the photo diode 242 is electrically connected to the circuit substrate 241 by using the lead 245. A light receiving surface of the photo diode 242 is approximately rectangular.

FIG. 7 is a schematic diagram showing layout of a first optical filter part and a second optical filter part in FIG. 5; As shown in FIG. 7, a plurality of first optical filter parts 243 and a plurality of second optical filter parts 244 are arranged in a matrix with a plurality of rows and columns. In the plurality of rows and columns, one first optical filter part 243 and one second optical filter part 244 are arranged alternately and cyclically in each row, and one first optical filter part 243 and one second optical filter part 244 are arranged alternately and cyclically in each column. In a thickness direction of the photo diode 242, a projection of the first optical filter part 243 on the photo diode 242 is a rectangle, and a projection of the second optical filter part 244 on the photo diode 242 is a rectangle. The first optical filter part 243 and the second optical filter part 244 have the same size. In other embodiments, shapes and arrangement rules of the first optical filter part 243 and the second optical filter part 244 are not limited thereto.

The photo diode 242 is configured to sense the light on the first band, the light on the second band, and the light on the third band. The first optical filter part 243 is configured to selectively transmit the light on the first band and the second band, and selectively block the light on the third band. The second optical filter part 244 is configured to selectively transmit the light on the third band, and selectively block the light on the first band and the light on the second band.

In some embodiments, the first band is on a red light spectrum (620 nm~780 nm), the second band is on an infrared light spectrum (780 nm~1 nm), and the third band is on a green light spectrum (490 nm~560 nm). That is, the red light, the infrared light, and the green light can be sensed by the photo diode 242. The first light filter part 243 may selectively transmit the red light and the infrared light and block the green light. The second optical filter unit 244 may selectively transmit the green light and block the red light and the infrared light. Therefore, a region that is of the photo diode 242 and that is covered by the first optical filter 243 may receive the red light and the infrared light, but receives no green light; and a region that is of the photo diode 242 and that is covered by the second optical filter 244 may receive the green light, but receives neither the red light nor the infrared light.

When the red light and the infrared light are irradiated to the photoelectric detector 24, the first optical filter part 243 may selectively transmit the red light and the infrared light, and the second optical filter part 244 may selectively block the red light and the infrared light. Therefore, a region covered by the first optical filter part 243 by the photo diode 242 is the most sensitive region for sensing the red light and the infrared light. When the oxygen saturation detection is performed by using the red light and the infrared light, a region in which the first optical filter part 243 is disposed in the photoelectric detector 24 is a main region for sensing the red light and the infrared light.

Similarly, when the green light is irradiated to the photoelectric detector 24, the second optical filter 244 may selectively transmit the green light, and the first optical filter 243 may selectively block the green light. Therefore, a region covered by the second optical filter part 244 by the photo diode 242 is the most sensitive region for sensing the green light. When the heart rate detection is performed by using the green light, a region in which the second optical filter 244 is disposed in the photoelectric detector 24 is a main region for sensing green light.

Therefore, when the PGG sensor in this embodiment of this application performs the heart rate detection by using the LED that emits green light, the photoelectric detector mainly performs sensing by using a region in which the second optical filter part is disposed (that is, a region most sensitive to green light). When the oxygen saturation detection is performed by using the LED that emits red light and the LED that emits infrared light, the photoelectric detector mainly performs sensing by using a region in which the first optical filter part is disposed (that is, the region that is most sensitive to the red light and the infrared light). In this way, the heart rate detection and the oxygen saturation detection in the photoelectric detector are relatively decoupled. This can achieve a high signal-to-noise ratio and improve detection accuracy.

Specifically, when the PPG sensor 20 detects the oxygen saturation by using the LED that emits red light and the LED that emits infrared light, red light and infrared light are reflected and absorbed by blood and a tissue of the human body to form attenuated light, and the attenuated light is received by the photo diode 242 through the first optical filter part 243. The photo diode 242 converts the received attenuated light into an electrical signal. After signal processing such as amplification and filtering is performed on the electrical signal, the first PPG signal and the second PPG signal are obtained. The processor may determine the ratio of oxygenated hemoglobin to hemoglobin based on the first PPG signal and the second PPG signal, and then calculate the oxygen saturation of a target part of the user. When the oxygen saturation detection is performed by using the red light and the infrared light, the green light is blocked by the first optical filter unit 243. This can reduce noise during oxygen saturation detection, and improve the signal-to-noise ratio of the oxygen saturation detection.

Similarly, when the PPG sensor 20 performs the heart rate detection by using the LED that emits green light, the green light is reflected and absorbed by blood and a tissue of the human body to form attenuated light, and the attenuated light is received by the photo diode 242 through the second optical filter 244. The photo diode 242 converts the received attenuated light into an electrical signal. After signal processing such as amplification and filtering is performed on the electrical signal, a third PPG signal is obtained. The processor determines the heart rate of the to-be-detected user based on the third PPG signal. When the heart rate detection is performed by using the green light, some infrared signals emitted by the human body and infrared signals of the external environment are blocked by the second optical filter 244. This can reduce noise in the heart rate detection, and improve the signal-to-noise ratio of the heart rate detection.

Figure 9:
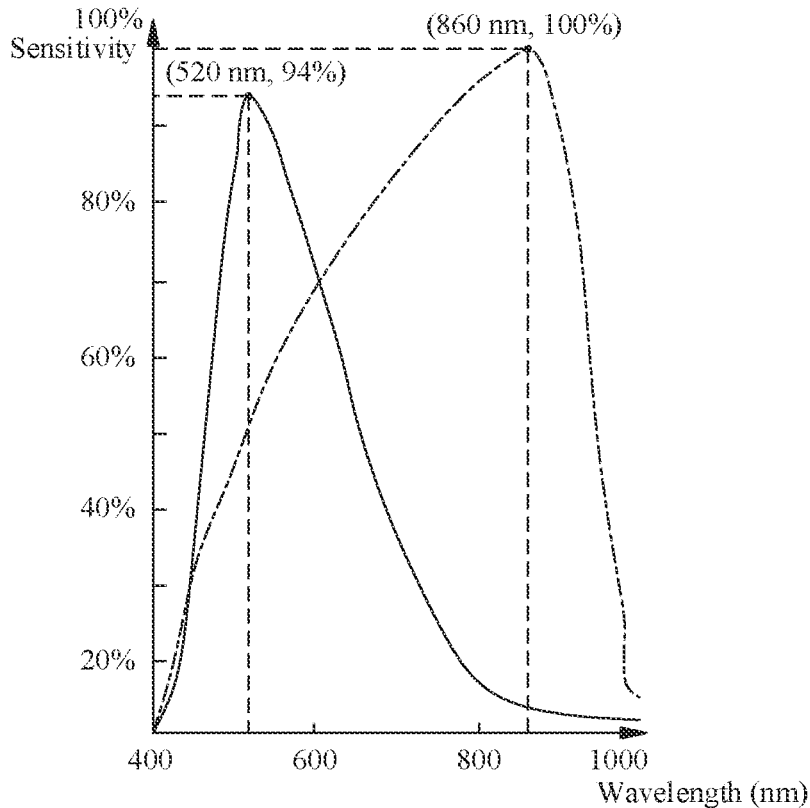
FIG. 9 is a schematic diagram showing a relationship between sensitivity of a photoelectric detector and a wavelength in FIG. 4.

It should be noted that the first optical filter part 243 and the second optical filter part 244 may be formed in a specific region of the photo diode 242 through film plating. The first optical filter part 243 may block green light through absorption or reflection. The second optical filter part 244 may block red light and infrared light through absorption or reflection. In some embodiments, the photo diode 242 is a full-spectrum sensitive photo diode, but sensitivity of the photo diode 242 to the red light and the infrared light is different from sensitivity of the photo diode 242 to the green light. Specifically, a ratio of the sensitivity of the photo diode 242 to the red light and the infrared light to sensitivity of the photo diode 242 to the green light is approximately (1.6~1.3): 1. To be specific, when a same photo diode 242 receives the red light and the infrared light at a light irradiance of 1 mW/cm$^2$, and receives the green light at a light irradiance of 1 mW/cm$^2$, a ratio of photo-generated current by the red light and the infrared light to photo-generated current by the green light is (1.6~1.3): 1. Therefore, in some embodiments, in a thickness direction of the photo diode 242, the ratio of the total area of projections of all the first optical filter parts 243 on the photo diode 242 to a total area of projections of all the second optical filter parts 244 on the photo diode 242 is 1:(1.6~1.3). In this way, the photo-generated current generated by the photoelectric detector 24 for the received red light and infrared light at a light irradiance of 1 mW/cm$^2$, is approximately equal to the photo-generated current generated by the photoelectric detector 24 for the received green light irradiated at a light irradiance of 1 mW/cm$^2$. As shown in FIG. 9, the sensitivity of the photoelectric detector 24 to the green light around 520 nm is approximately equal to sensitivity of the photoelectric detector 24 to the infrared light around 860 nm.

In some embodiments, the ratio of the total area of the projections of all the second optical filter parts 244 on the photodiode 242 to the total area of the projections of all the first optical filter parts 243 on the photodiode 242 is, for example, (1.6:1), (1.5:1), (1.4:1), or (1.3:1). When the ratio is 1.5:1, sensitivity of the photoelectric detector to green light around 520 nm is closest to sensitivity of the photoelectric detector to infrared light around 860 nm. Specifically, by making the total area of the projections of the first optical filter parts 243 on the photodiode 242 smaller than the total area of the projections of the second optical filter parts 244 on the photodiode 242, when the PPG sensor 20 performs the heart rate detection by using the LED that emits green light, even if some infrared signals emitted by the human body and some infrared signals in the external environment are incident into the first optical filter part 243 and are sensed by the photodiode 242, because the total area of the projections of all the first optical filter parts 243 on the photodiode 242 and the total area of the projections of all the second optical filter parts 244 on the photodiode 242 are small, after the photodiode 242 receives the infrared signals emitted by the human body and the infrared signals in the external environment, a photo-generated current corresponding to the infrared signals emitted by the human body and the infrared signals in the external environment is small. This can reduce the noise in the heart rate detection, and increase a signal-to-noise ratio of the heart rate detection.

In some embodiments, an area of a projection of each first optical filter part 243 on the photodiode 242 is the same as an area of a projection of each second optical filter part 244 on the photodiode 242. By adjusting a ratio of a quantity of the first optical filter parts 243 to a quantity of the second optical filter parts 244, the ratio of the total area of projections of all first optical filter parts 243 on the photodiode 242 to a total area of projections of all second optical filter parts 244 on the photodiode 242 is 1:(1.6~1.3).

In some other embodiments, the first optical filter part 243 and the second optical filter part 244 are the same. A ratio of an area of a projection of each first optical filter part 243 on the photodiode 242 to an area of a projection of each second optical filter part 244 on the photodiode 242 may be adjusted, so that the ratio of the total area of projections of all the first optical filter parts 243 on the photodiode 242 to a total area of projections of all the second optical filter parts 244 on the photodiode 242 is 1:(1.6~1.3).

Figure 8:
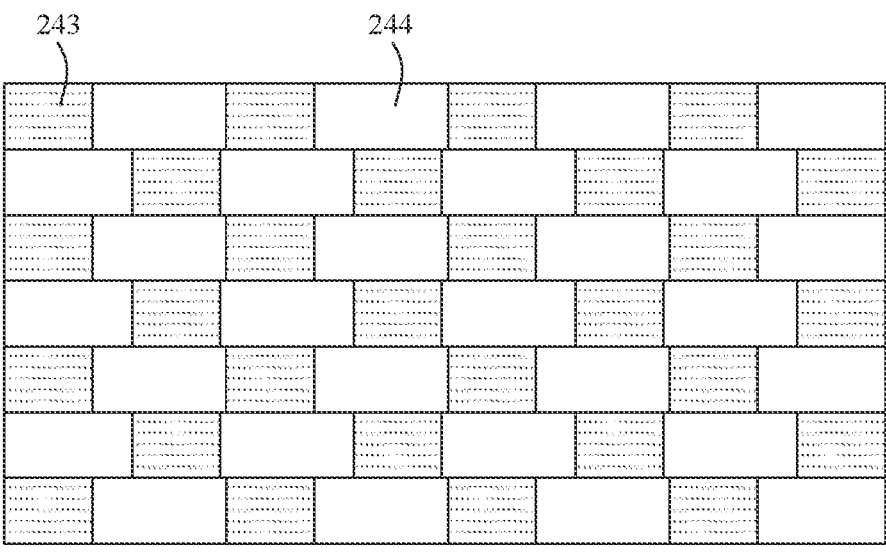
FIG. 8 is a schematic diagram showing layout of a first optical filter part and a second optical filter part according to another embodiment of this application.

Specifically, as shown in FIG. 8, a plurality of first optical filter parts 243 and a plurality of second optical filter parts 244 are arranged in a matrix with a plurality of rows and columns. In the plurality of rows and columns, one first optical filter part 243 and one second optical filter part 244 are arranged alternately and cyclically in each row, and one first optical filter part 243 and one second optical filter part 244 are arranged alternately and cyclically in each column. A quantity of the first optical filter parts 243 and a quantity of the second optical filter parts 244 are the same. Both the projection of the first optical filter part 243 on the photo diode 242 and the projection of the second optical filter part 244 on the photo diode 242 are rectangular, and a width of the first optical filter part 243 is the same as a width of the second optical filter part 244. Therefore, the ratio of the length of the first filter part 243 to the length of the second filter part 244 may be adjusted to 1:(1.6~1.3), so that the ratio of the total area of the projections of all the first filter parts 243 on the photodiode 242 to the total area of the projections of all the second filter parts 244 on the photodiode 242 is 1:(1.6~1.3).

In other embodiments, shapes and arrangement rules of the first optical filter part 243 and the second optical filter part 244 are not limited thereto. For example, the quantity of the first optical filter parts 243 and the quantity of the second optical filter parts 244 are different, and the area of each first optical filter part 243 and the area of each second optical filter part 244 are also different. However, the ratio of the total area of the projections of all the first optical filter parts 243 on the photodiode 242 to the total area of the projections of all the second optical filter parts 244 on the photodiode 242 is 1:(1.6~1.3).

According to the PPG sensor in this embodiment of this application, a photo diode is sensitive to a plurality of bands (a red light band, a green light band, and an infrared light band); and the first optical filter is disposed to selectively transmit red light and infrared light, and the second optical filter is disposed to selectively transmit green light. Compared with the conventional technology shown in FIG. 1, in the PPG sensor in this embodiment of this application, the heart rate detection and the oxygen saturation detection in the photoelectric detector are relatively decoupled. This can achieve a high signal-to-noise ratio and improve detection accuracy. In addition, compared with the conventional technology shown in FIG. 2, in a case in which a same plate area is occupied, when the PPG sensor in this embodiment of this application detects the heart rate by using the green light and detects the oxygen saturation by using the red light and the infrared light, an effective sensing area is larger, and the signal-to-noise ratio is higher. For example, when the heart rate detection is performed by using the green light, only a PD2 circled by a dashed line in the PPG sensor shown in FIG. 2 is used for detection, but two PD1 covered by the dashed line cannot sense the green light, and an effective sensing area of the PPG sensor is an overall photosensitive area (set as A) of the PD2. In the PPG sensor in this embodiment of this application, as shown in FIG. 4, all three photoelectric detectors 24 circled by a dashed line can sense the green light. If an area of a region that can effectively sense the green light in each photoelectric detector 24 is the same as an area of a region that can effectively sense the red light and the infrared light, in this embodiment of this application, an area of the region that can effectively sense the green light and that is of the PPG sensor 20 is A×50%× 3=1.5A. This enhances a sensed signal value of the green light sensed by the PPG sensor 20, and improves a signal-to-noise ratio of the heart rate detection.

In other embodiments, in the plurality of photoelectric detectors included in the PPG sensor, for different photoelectric detectors, the ratio of the total area of the projections of the first optical filter parts on the photo diode to the total area of the projections of all the second filter optical filter parts on the photodiode may be different. The processor of the electronic device may process the PPG signals generated by one or more photoelectric detectors. For example, in some photoelectric detectors, a total area of all the first optical filter parts is larger than or equal to a total area of all the second optical filter parts, and the some photoelectric detectors (for ease of description, these photoelectric detectors are defined as first photoelectric detectors) are more sensitive to the red light and the infrared light than to the green light. In some other photoelectric detectors, the total area of all the first optical filter parts is smaller than the total area of all the second optical filter parts, and the some other photoelectric detectors (for ease of description, these photoelectric detectors are defined as second photoelectric detectors) are more sensitive to the green light than to the red light and the infrared light.

Specifically, in a scenario in which the user detects the oxygen saturation by using the electronic apparatus, the processor of the electronic apparatus may select to enable the first photoelectric detector that is more sensitive to the red light and the infrared light, and disable the second photoelectric detector, so as to improve accuracy of the oxygen saturation detection by using the first photoelectric detector that is more sensitive to the red light and the infrared light. Similarly, in a scenario in which the user detects the heart rate by using the electronic apparatus, the processor of the electronic apparatus may select to enable a second photoelectric detector that is more sensitive to the heart rate, and disable the first photoelectric detector, so as to improve accuracy of the heart rate detection by using the second photoelectric detector that is more sensitive to the heart rate. It can be understood that, in a scenario in which the user detects the heart rate (or the oxygen saturation) by using the electronic apparatus, the processor of the electronic apparatus may also enable the first photoelectric detectors and the second photoelectric detectors at the same time, and the heart rate (or oxygen saturation) is detected by performing a processing operation on PPG signals generated by the plurality of first photoelectric detectors and the plurality of second photoelectric detectors.

In addition, it should be noted that the PPG sensor is not limited to being applied to a smartwatch. For example, the PPG sensor may be further applied to a smart band. Alternatively, the PPG sensor may surrounds another human body part (for example, a head, an ankle, or a finger) of the user for being applied to another wearable apparatus. Another wearable apparatus is, for example, a head mounted device (for example, a smart helmet), or a clothing-type device (for example, smart clothing, a smart glove, or a smart arm band).

More specifically, the PPG sensor may be attached or integrated to shoes, socks, ties, sleeves or collars of shirts, pants, or belts of skirts of a user. Further, the PPG sensor may be removed from the shoes or clothing of the user. For example, when the PPG sensor is used to detect physiological characteristics of the user, the PPG sensor may be attached to the shoes or clothing of the user. After the detection is completed, the PPG sensor may be removed from the shoes or clothing of the user. In this way, locations to which the PGG sensor needs to be attached may be selected for different users and/or different human body parts of a same user, so that application scenarios of the PPG sensor are diversified and flexible.

In addition, the PPG sensor may also be applied to a device that has a health detection function, for example, an oxygen saturation meter or a heart rate detector, but this is not limited herein.

The foregoing implementations are merely used to describe the technical solutions of this application, but are not limited thereto. Although this application is described in detail with reference to the foregoing preferred implementations, persons of ordinary skill in the art should understand that modification or equivalent replacement of the technical solutions of this application may be performed without departing from the spirit and scope of the technical solutions of this application.

What is claimed is:

1. A photoelectric detector, comprising:
a photo diode, configured to sense light on a first band, a second band, and a third band;
at least one first optical filter part, located on the photo diode, and configured to transmit light on the first band and the second band and block light on the third band; and
at least one second optical filter part, located on the photo diode, configured to transmit the light on the third band and block the light on the first band and the second band, and
wherein a plurality of first optical filters and a plurality of second optical filters are arranged in a matrix with a plurality of rows and columns, and in the plurality of rows and columns, one first optical filter part and one second optical filter part are arranged alternately and cyclically in each row, and one first optical filter part and one second optical filter part are arranged alternately and cyclically in each column.

2. The photoelectric detector according to claim 1, wherein the first band is in a red light spectrum, the second band is in an infrared light spectrum, and the third band is in a green light spectrum.

3. The photoelectric detector according to claim 1, wherein in a thickness direction of the photo diode, a ratio of an area of a projection of the at least one first optical filter part on the photo diode to an area of a projection of the at least one second optical filter part on the photo diode is 1:(1.6~1.3).

4. The photoelectric detector according to claim 3, wherein a quantity of the first optical filter parts and a quantity of the second optical filter parts are the same, and in the thickness direction of the photo diode, the ratio of the an area of a projection of each first optical filter part on the photo diode to a an area of a projection of each second optical filter part on the photo diode is 1:(1.6~1.3).

5. The photoelectric detector according to claim 3, wherein in the thickness direction of the photo diode, an area of each projection of the first optical filter part on the photo diode is the same as an area of each projection of the second optical filter part on the photo diode, and a ratio of a quantity of the first optical filter parts to a quantity of the second optical filter parts is 1:(1.6~1.3).

6. The photoelectric detector according to claim 1, wherein in a thickness direction of the photo diode, a projection of the first optical filter part on the photo diode is a rectangle, and a projection of the second optical filter part on the photo diode is a rectangle.

7. The photoelectric detector according to claim 6, wherein in the thickness direction of the photo diode, a width of the rectangle formed by the projection of the first optical filter part on the photo diode is the same as a width of the rectangle formed by the projection of the second optical filter part on the photo diode.

8. A photo plethysmo graph (PPG) sensor, comprising:
a photoelectric detector, comprising
a photo diode, configured to sense light on a first band, a second band, and a third band;
at least one first optical filter part, located on the photo diode, and configured to transmit light on the first band and the second band and block light on the third band; and
at least one second optical filter part, located on the photo diode, configured to transmit the light on the third band and block the light on the first band and the second band, and
wherein a plurality of first optical filters and a plurality of second optical filters are arranged in a matrix with a plurality of rows and columns, and in the plurality of rows and columns, one first optical filter part and one second optical filter part are arranged alternately and cyclically in each row, and one first optical filter part and one second optical filter part are arranged alternately and cyclically in each column;
a first light source, configured to send a first optical signal, wherein at least a part of light obtained after the first optical signal is reflected by skin or tissue of a user is on the first band;
a second light source, configured to send a second optical signal, wherein at least a part of light obtained after the second optical signal is reflected by the skin or tissue of the user is on the second band; and
a third light source, configured to send a third optical signal, wherein at least a part of light obtained after the third optical signal is reflected by the skin or tissue of the user is on the third band; wherein
the photoelectric detector is configured to receive light on the first band and generate a first PPG signal, receive light on the second band and generate a second PPG signal, and receive light on the third band and generate a third PPG signal, wherein the first PPG signal, the second PPG signal, and the third PPG signal are used to detect physiological characteristics of the user.

9. The PPG sensor according to claim 8, wherein the PPG sensor comprises a light source group, the light source group comprises a first light source, a second light source, and a third light source, and a plurality of photoelectric detectors are spaced around the light source group.

10. The PPG sensor according to claim 9, wherein the PPG sensor comprises a plurality of light source groups that are spaced.

11. The PPG sensor according to claim 8, wherein the physiological characteristics comprise oxygen saturation and a heart rate; the first optical signal is red light, the second optical signal is infrared light, and the first PPG signal and the second PPG signal are used to detect the oxygen saturation of the user; and the third optical signal is green light, and the third PPG signal is used to detect the heart rate of the user.

12. The PPG sensor according to claim 8, wherein the first band is in a red light spectrum, the second band is in an infrared light spectrum, and the third band is in a green light spectrum.

13. The PPG sensor according to claim 8, wherein in a thickness direction of the photo diode, a ratio of an area of a projection of the at least one first optical filter part on the photo diode to an area of a projection of the at least one second optical filter part on the photo diode is 1:(1.6~1.3).

14. The PPG sensor according to claim 13, wherein a quantity of the first optical filter parts and a quantity of the second optical filter parts are the same, and in the thickness direction of the photo diode, the ratio of the an area of a projection of each first optical filter part on the photo diode to a an area of a projection of each second optical filter part on the photo diode is 1:(1.6~1.3).

15. The PPG sensor according to claim 13, wherein in the thickness direction of the photo diode, an area of each projection of the first optical filter part on the photo diode is the same as an area of each projection of the second optical filter part on the photo diode, and a ratio of a quantity of the first optical filter parts to a quantity of the second optical filter parts is 1:(1.6~1.3).

16. The PPG sensor according to claim 8, wherein in a thickness direction of the photo diode, a projection of the first optical filter part on the photo diode is a rectangle, and a projection of the second optical filter part on the photo diode is a rectangle.

17. The PPG sensor according to claim 16, wherein in the thickness direction of the photo diode, a width of the rectangle formed by the projection of the first optical filter part on the photo diode is the same as a width of the rectangle formed by the projection of the second optical filter part on the photo diode.

18. An electronic device, comprising a photo plethysmo graph (PPG) sensor, comprising:

a photoelectric detector, comprising a photo diode, configured to sense light on a first band, a second band, and a third band;

at least one first optical filter part, located on the photo diode, and configured to transmit light on the first band and the second band and block light on the third band; and at least one second optical filter part, located on the photo diode, configured to transmit the light on the third band and block the light on the first band and the second band, and wherein a plurality of first optical filters and a plurality of second optical filters are arranged in a matrix with a plurality of rows and columns, and in the plurality of rows and columns, one first optical filter part and one second optical filter part are arranged alternately and cyclically in each row, and one first optical filter part and one second optical filter part are arranged alternately and cyclically in each column;

a first light source, configured to send a first optical signal, wherein at least a part of light obtained after the first optical signal is reflected by skin or tissue of a user is on the first band;

a second light source, configured to send a second optical signal, wherein at least a part of light obtained after the second optical signal is reflected by the skin or tissue of the user is on the second band; and a third light source, configured to send a third optical signal, wherein at least a part of light obtained after the third optical signal is reflected by the skin or tissue of the user is on the third band; wherein the photoelectric detector is configured to receive light on the first band and generate a first PPG signal, receive light on the second band and generate a second PPG signal, and receive light on the third band and generate a third PPG signal, wherein the first PPG signal, the second PPG signal, and the third PPG signal are used to detect physiological characteristics of the user.

19. The electronic device according to claim 18, wherein the first band is in a red light spectrum, the second band is in an infrared light spectrum, and the third band is in a green light spectrum.

20. The electronic device according to claim 18, wherein in a thickness direction of the photo diode, a ratio of an area of a projection of the at least one first optical filter part on the photo diode to an area of a projection of the at least one second optical filter part on the photo diode is 1:(1.6~1.3).

\*    \*    \*    \*    \*